United States Patent
Filippini et al.

(10) Patent No.: US 6,210,930 B1
(45) Date of Patent: Apr. 3, 2001

(54) PROCESS FOR PREPARING DOXORUBICIN

(75) Inventors: Silvia Filippini, Milan (IT); Natalia Lomovskaya; Leonid Fonstein, both of Madison, WI (US); Anna Luisa Colombo, Milan (IT); C. Richard Hutchinson, Cross Plains, WI (US); Sharee L. Otten, Madison, WI (US); Umberto Breme, Vigevano (IT)

(73) Assignee: Pharmacia & Upjohn, S.P.A., Milan (IT)

( * ) Notice: Subject to any disclaimer, the term of this patent is extended or adjusted under 35 U.S.C. 154(b) by 0 days.

(21) Appl. No.: 09/180,271
(22) PCT Filed: Mar. 5, 1998
(86) PCT No.: PCT/US98/03938
§ 371 Date: Jan. 14, 1999
§ 102(e) Date: Jan. 14, 1999
(87) PCT Pub. No.: WO98/39458
PCT Pub. Date: Sep. 11, 1998

Related U.S. Application Data

(63) Continuation-in-part of application No. 08/901,306, filed on Jul. 28, 1997, now Pat. No. 5,955,319, and a continuation-in-part of application No. 08/812,412, filed on Mar. 6, 1997, now Pat. No. 5,989,869.

(51) Int. Cl.[7] ................ C12P 19/56; C12N 9/02; C12N 15/53; C12N 15/63; C12N 15/74
(52) U.S. Cl. ............ 435/78; 435/189; 435/252.35; 435/320.1; 435/471; 536/23.2
(58) Field of Search ............ 435/78, 471, 187, 435/189, 252.3, 252.35, 320.1; 536/23.2

(56) References Cited

U.S. PATENT DOCUMENTS

| | | | |
|---|---|---|---|
| 4,592,999 | * 6/1986 | Umezawa et al. | 435/78 |
| 5,364,781 | * 11/1994 | Hutchinson et al. | 435/193 |
| 5,563,064 | * 10/1996 | Hutchinson et al. | 435/252.3 |
| 5,652,125 | * 7/1997 | Scotti et al. | 435/78 |
| 5,665,564 | * 9/1997 | Caruso et al. | 345/69.1 |
| 5,695,966 | * 12/1997 | Inventi et al. | 435/78 |
| 5,786,190 | * 7/1998 | Inventi et al. | 435/183 |
| 5,843,735 | * 12/1998 | Lee et al. | 435/172.1 |
| 5,955,319 | * 9/1999 | Filippini et al. | 435/78 |
| 5,962,293 | * 11/1999 | Strohl et al. | 435/189 |
| 5,976,830 | * 11/1999 | Strohl et al. | 435/41 |
| 5,989,869 | * 11/1999 | Filippini et al. | 435/78 |

OTHER PUBLICATIONS

Stutzman–Engwall, K. J., et al., 1989, "Multigene families for anthracycline antibiotic production in Streptomyces peucetius", Proceedings of the National Academy of Sciences, U.S.A., vol. 86, pp. 3135–3139.*

Otten, S. L., et al., 1990, "Cloning and expression of daunorubicin biosynthesis genes from Streptomyces peucetius subsp. caesius", Journal of Bacteriology, vol. 172, pp. 3247–3434.*

Hwang, C.K., et al. 1995, "Expression of Streptomyces peucetius genes for doxorubicin resistance and aklavinone 11–hydroxylase in Streptomyces galilaeus ATCC 3233 . . . ", Antimicrobial Agents and Chemotherapy, vol. 39, pp. 1616–1620.*

Lomoskaya, N., et al., 1996, "The Streptomyces peucetius drrC gene encodes a UvrA–like protein involved in daunorubicin resistance and production", Journal of Bacteriology, vol. 178, pp. 3238–3245.*

Dickens, M. L., et al., 1996, "Cloning, sequencing, and analysis of aklaviketone reductase from Streptomyces sp. strain C5", Journal of Bacteriology, vol. 178, pp. 3384–3388.*

Dickens, M. L., et al., 1996, "Isolation and characterization of a gene from Streptomyces sp. strain C5 that confers the abilitiy to convert daunomycin to doxorubicin on Streptomyces lividans TK4", Journal of Bacteriology, vol. 178, pp. 3389–3395.*

Scotti, C., et al., 1996, "Enhanced antibiotic production by manipulation of the Streptomyces peucetius dnrH and dnmT involved in doxorubicin (adriamycin) biosynthesis", *Journal of Bacteriology,* vol. 178, pp. 7316–7321.*

Kaur, P., 1997, "Expression and characterization of DrrA and DrrB proteins of Streptomyces peucetius in Escherichia coli: DrrA is an ATP binding protein", *Journal of Bacteriology,* vol. 179, pp. 569–575.*

* cited by examiner

*Primary Examiner*—Charles L. Patterson, Jr.
*Assistant Examiner*—William. M. Moore
(74) *Attorney, Agent, or Firm*—Arent Fox Kintner Plotkin & Kahn, PLC

(57) ABSTRACT

The present invention is directed to a process for improving daunorubicin and doxorubicin production by means of a recombinant microorganism in which a gene of daunorubicin metabolism is mutated. The mutated gene is preferably dnrU and/or dnrX.

CH₃CH₂COSoA
+
9 CH₂COSCoA
|
CO₂H

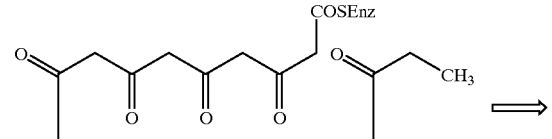

Decapolyketide

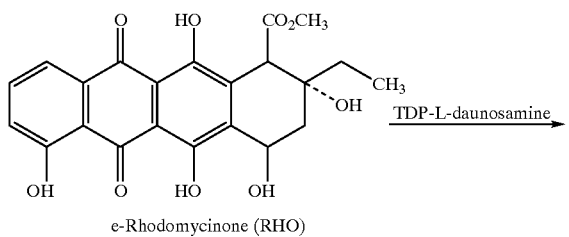

ε-Rhodomycinone (RHO)

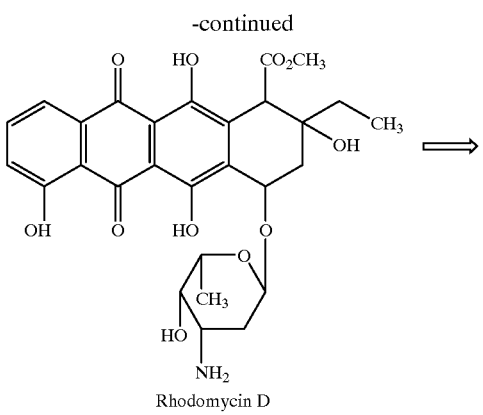

Rhodomycin D

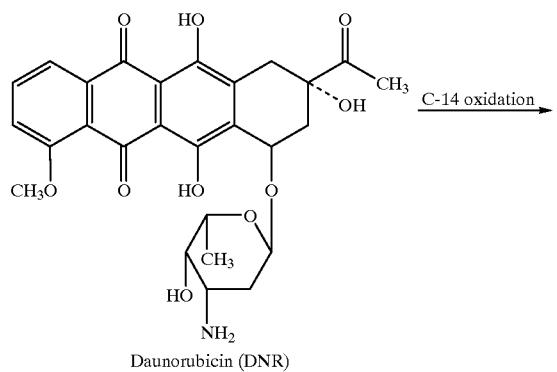

Daunorubicin (DNR)

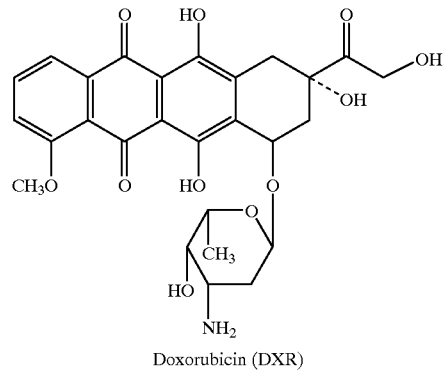

Doxorubicin (DXR)

16 Claims, 6 Drawing Sheets

Sequence ID NO: 3

SstI
ATGGCTGAGCTCAGCCTGGCGGAACTGCGGGAGATCATGCGGCAGAGCCTGGGGGAGGACGAGGTCCCCGACCTTGCGGACGCGGACACCGTGACCTTCG
dpsG>
M  A  E  L  S  L  A  E  L  R  E  I  M  R  Q  S  L  G  E  D  E  V  P  D  L  A  D  A  D  T  V  T  F  E
AGGACCTCGGGCTCGACTCCCTGGCCGTCCTGGAAACGGTCAACCACATCGAGCGGACCTATGGCGTGAAGCTGCCCGAGGAGAACTGGCGGACGTCAG
 D  L  G  L  D  S  L  A  V  L  E  T  V  N  H  I  E  R  T  Y  G  V  K  L  P  E  E  L  A  E  V  R
GACGCCGCATAGCATGCTGATCTTCGTCAACGAGAGGCTGCGAGCGGCATGACGGCCTCCACCCCGCACCACGGGACACCACCGGGGCCGGCCTGTCGG
 T  P  H  S  M  L  I  F  V  N  E  R  L  R  A  A  A  dnrU>M  T  A  S  T  P  H  H  G  T  P  R  G  G  L  S  G
GCCGGACGGTGCTGGTCACCGGGGCCACGTCCGGCATCGGCCGGGCGGCCCTCGCGGTGGCCCAGGGGGCCCGGTCGTCCGCGTCGTGCTCGTGGCCGGA
 R  T  V  L  V  T  G  A  T  S  G  I  G  R  A  A  A  L  A  V  A  R  Q  G  A  R  V  V  L  V  G  R  D
CCCGAGCGTCTGCCGGACCGTCACGACGAGGTGGCCCGGACCGCCCGGCGCCCTTCCGCGGGACTTCGCCGAGCTGCGCCAGGTACGC
 R  T  V  T  M  E  V  A  R  T  A  G  P  A  P  D  A  F  R  A  D  F  A  E  L  R  Q  V  R
 P  E  R  L  R  T  V  T  M  E  V  A  R  T  A  G  P  A  P  D  A  F  R  A  D  F  A  E  L  R  Q  V  R

Fig. 2A

| Fig. 2A |
|---------|
| Fig. 2B |

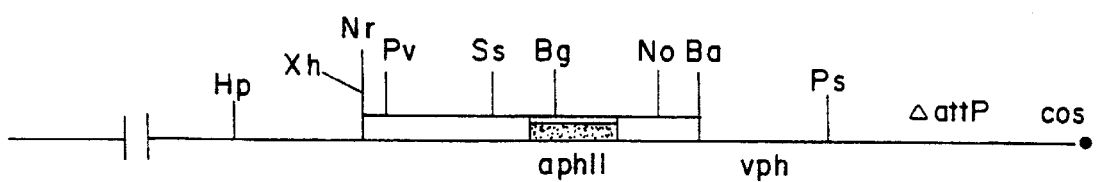
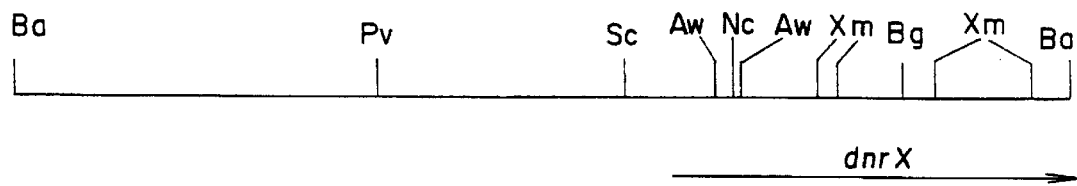
Fig. 4
Fig. 5

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 864 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: CDS
      (B) LOCATION: 1..861

(xi) SEQUENCE DESCRIPTION: SEQ ID NO:1:

```
ATG ACG GCC TCC ACC CCG CAC CAC GGG ACA CCA CGC GGC GGC CTG TCG      48
Met Thr Ala Ser Thr Pro His His Gly Thr Pro Arg Gly Gly Leu Ser
 1               5                  10                  15
```

```
GGC CGG ACG GTG CTG GTC ACC GGG GCC ACG TCC GGC ATC GGC CGG GCG        96
Gly Arg Thr Val Leu Val Thr Gly Ala Thr Ser Gly Ile Gly Arg Ala
         20                  25                  30

GCG GCC CTC GCG GTC GCC CGC CAG GGG GCC CGC GTC GTG CTC GTC GGC       144
Ala Ala Leu Ala Val Ala Arg Gln Gly Ala Arg Val Val Leu Val Gly
     35                  40                  45

CGG GAC CCC GAG CGT CTG CGG ACC GTC ACG AAC GAG GTG GCC CGG ACC       192
Arg Asp Pro Glu Arg Leu Arg Thr Val Thr Asn Glu Val Ala Arg Thr
 50                  55                  60

GCC GGC CCG GCC CCG GAC GCC TTC CGC GCG GAC TTC GCC GAG CTG CGC       240
Ala Gly Pro Ala Pro Asp Ala Phe Arg Ala Asp Phe Ala Glu Leu Arg
 65                  70                  75                  80

CAG GTA CGC GAC CTG GGG GAG CGG CTG CGG GAC CGG TAC CCG CGC ATC       288
Gln Val Arg Asp Leu Gly Glu Arg Leu Arg Asp Arg Tyr Pro Arg Ile
             85                  90                  95

GAT GTC ATG GCC AGC AAC GCC GGC GGC ATG TTC TGG TCG CGC ACC ACG       336
Asp Val Met Ala Ser Asn Ala Gly Gly Met Phe Trp Ser Arg Thr Thr
                100                 105                 110

ACC CAG GAC GGG TTC GAG GCC ACC ATC CAG GTC AAT CAC CTC GCA GGC       384
Thr Gln Asp Gly Phe Glu Ala Thr Ile Gln Val Asn His Leu Ala Gly
            115                 120                 125

TTC CTG CTG GCA CGG CTG CTG CGG GAG CGG CTC GCG GGC GGG CGG CTG       432
Phe Leu Leu Ala Arg Leu Leu Arg Glu Arg Leu Ala Gly Gly Arg Leu
130                 135                 140

ATC CTC ACC TCG TCC GAC GCG TAC ACC CAG GGC CGG ATC GAC CCG GAC       480
Ile Leu Thr Ser Ser Asp Ala Tyr Thr Gln Gly Arg Ile Asp Pro Asp
145                 150                 155                 160

GAC CTC AAC GGC GAC CGT CAC CGC TAC AGC GCC GGC CAG GCG TAC GGC       528
Asp Leu Asn Gly Asp Arg His Arg Tyr Ser Ala Gly Gln Ala Tyr Gly
                165                 170                 175

ACG TCC AAA CAG GCC AAC ATC ATG ACC GCG GCG GAG GCC GCC AGG CGC       576
Thr Ser Lys Gln Ala Asn Ile Met Thr Ala Ala Glu Ala Ala Arg Arg
            180                 185                 190

TGG CCG GAC GTG CTG GCG GTC AGC TAT CAC CCC GGT GAG GTC CGC ACC       624
Trp Pro Asp Val Leu Ala Val Ser Tyr His Pro Gly Glu Val Arg Thr
        195                 200                 205

CGC ATC GGA CGG GGC ACG GTC GCC TCG TCC TAC TTC CGG TTC AAC CCC       672
Arg Ile Gly Arg Gly Thr Val Ala Ser Ser Tyr Phe Arg Phe Asn Pro
    210                 215                 220

TTC CTG CGC TCC GCG GCG AAG GGC GCC GAC ACC CTC GTG TGG CTG GCG       720
Phe Leu Arg Ser Ala Ala Lys Gly Ala Asp Thr Leu Val Trp Leu Ala
225                 230                 235                 240

TCC GCG CCG GCC GAG GAG TTG ACC ACG GGC GGC TAC TAC AGC GAC CGG       768
Ser Ala Pro Ala Glu Glu Leu Thr Thr Gly Gly Tyr Tyr Ser Asp Arg
                245                 250                 255

CGG CTG TCC CCG GTG AGC GGC CCG ACC GCC GAC GCC GGC CTC GCG GCG       816
Arg Leu Ser Pro Val Ser Gly Pro Thr Ala Asp Ala Gly Leu Ala Ala
            260                 265                 270

AAG CTC TGG GAG GCC GGC GCG GCC GCC GTC GGC GAC ACC GCG CAC           861
Lys Leu Trp Glu Ala Gly Ala Ala Ala Val Gly Asp Thr Ala His
        275                 280                 285

TGA                                                                   864
```

(2) INFORMATION FOR SEQ ID NO:2:

(i) SEQUENCE CHARACTERISTICS:
        (A) LENGTH: 287 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:2:

```
Met Thr Ala Ser Thr Pro His His Gly Thr Pro Arg Gly Gly Leu Ser
1               5                   10                  15

Gly Arg Thr Val Leu Val Thr Gly Ala Thr Ser Gly Thr Gly Arg Ala
            20                  25                  30

Ala Ala Leu Ala Val Ala Arg Gln Gly Ala Arg Val Val Leu Val Gly
            35                  40                  45

Arg Asp Pro Glu Arg Leu Arg Thr Val Thr Asn Glu Val Ala Arg Thr
50                  55                  60

Ala Gly Pro Ala Pro Asp Ala Phe Arg Ala Asp Phe Ala Glu Leu Arg
65                  70                  75                  80

Gln Val Arg Asp Leu Gly Glu Arg Leu Arg Asp Arg Tyr Pro Arg Ile
            85                  90                  95

Asp Val Met Ala Ser Asn Ala Gly Gly Met Phe Trp Ser Arg Thr Thr
            100                 105                 110

Thr Gln Asp Gly Phe Glu Ala Thr Ile Gln Val Asn His Leu Ala Gly
            115                 120                 125

Phe Leu Leu Ala Arg Leu Leu Arg Glu Arg Leu Ala Gly Gly Arg Leu
130                 135                 140

Ile Leu Thr Ser Ser Asp Ala Tyr Thr Gln Gly Arg Ile Asp Pro Asp
145                 150                 155                 160

Asp Leu Asn Gly Asp Arg His Arg Tyr Ser Ala Gly Gln Ala Tyr Gly
            165                 170                 175

Thr Ser Lys Gln Ala Asn Ile Met Thr Ala Ala Glu Ala Ala Arg Arg
            180                 185                 190

Trp Pro Asp Val Leu Ala Val Ser Tyr His Pro Gly Glu Val Arg Thr
            195                 200                 205

Arg Ile Gly Arg Gly Thr Val Ala Ser Ser Tyr Phe Arg Phe Asn Pro
210                 215                 220

Phe Leu Arg Ser Ala Ala Lys Gly Ala Asp Thr Leu Val Trp Leu Ala
225                 230                 235                 240

Ser Ala Pro Ala Glu Glu Leu Thr Thr Gly Gly Tyr Tyr Ser Asp Arg
            245                 250                 255

Arg Leu Ser Pro Val Ser Gly Pro Thr Ala Asp Ala Gly Leu Ala Ala
            260                 265                 270

Lys Leu Trp Glu Ala Gly Ala Ala Val Gly Asp Thr Ala His
            275                 280                 285
```

(2) INFORMATION FOR SEQ ID NO:3:

(i) SEQUENCE CHARACTERISTICS:
            (A) LENGTH: 1569 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:3:

```
ATGGCTGAGC TCAGCCTGGC GGAACTGCGG GAGATCATGC GGCAGAGCCT GGGGGAGGAC      60

GAGGTCCCCG ACCTTGCGGA CGCGGACACC GTGACCTTCG AGGACCTCGG GCTCGACTCC     120

CTGGCCGTCC TGGAAACGGT CAACCACATC GAGCGGACCT ATGGCGTGAA GCTGCCCGAG     180

GAGGAACTGG CGGAGGTCAG GACGCCGCAT AGCATGCTGA TCTTCGTCAA CGAGAGGCTG     240
```

-continued

```
CGAGCGGCGG CATGACGGCC TCCACCCCGC ACCACGGGAC ACCACGCGGC GGCCTGTCGG      300

GCCGGACGGT GCTGGTCACC GGGGCCACGT CCGGCATCGG CCGGGCGGCG GCCCTCGCGG      360

TCGCCCGCCA GGGGGCCCGC GTCGTGCTCG TCGGCCGGGA CCCCGAGCGT CTGCGGACCG      420

TCACGAACGA GGTGGCCCGG ACCGCCGGCC CGGCCCCGGA CGCCTTCCGC GCGGACTTCG      480

CCGAGCTGCG CCAGGTACGC GACCTGGGGG AGCGGCTGCG GGACCGGTAC CCGCGCATCG      540

ATGTCATGGC CAGCAACGCC GGCGGCATGT TCTGGTCGCG CACCACGACC CAGGACGGGT      600

TCGAGGCCAC CATCCAGGTC AATCACCTCG CAGGCTTCCT GCTGGCACGG CTGCTGCGGG      660

AGCGGCTCGC GGGCGGGCGG CTGATCCTCA CCTCGTCCGA CGCGTACACC CAGGGCCGGA      720

TCGACCCGGA CGACCTCAAC GGCGACCGTC ACCGCTACAG CGCCGGCCAG GCGTACGGCA      780

CGTCCAAACA GGCCAACATC ATGACCGCGG CGGAGGCCGC CAGGCGCTGG CCGGACGTGC      840

TGGCGGTCAG CTATCACCCC GGTGAGGTCC GCACCCGCAT CGGACGGGGC ACGGTCGCCT      900

CGTCCTACTT CCGGTTCAAC CCCTTCCTGC GCTCCGCGGC GAAGGGCGCC GACACCCTCG      960

TGTGGCTGGC GTCCGCGCCG GCCGAGGAGT TGACCACGGG CGGCTACTAC AGCGACCGGC     1020

GGCTGTCCCC GGTGAGCGGC CCGACCGCCG ACGCCGGCCT CGCGGCGAAG CTCTGGGAGG     1080

CCGGCGCGGC CGCCGTCGGC GACACCGCGC ACTGACGGCG GCGGCCCGCC CGCCCGCAT     1140

GTCCGTCTCA TCCGCGAGAT GTCCGTCTCA TCCGCGAGCG CAGACGCTCG TGTGCCGATC     1200

CATCGAAAGG AACGATTCGT GACCAGGTTC GCGCCCGGCG CCCCCGCATG GTTCGACCTC     1260

GGTTCGCCCG ATGTCGCCGC CTCGGCCGAC TTCTACACCG GCCTGTTCGG CTGGACCGCC     1320

ACCGTGGTCA GCGACCCGGG CGCCGGGGGA TGCACGACGT TCAGCTCCGA CGGGAAGCTG     1380

GTCGCCGCGG TCGCCCGCCA CCAGATCGAC ACCCCCTACC ACCGGCCGTA CGGGCCCGGG     1440

AACGACCAGC ACGGCATGCC GGCCATCTGG ACCGTGTACT CGCCACCGA CGACGCCGAC     1500

GCACTGACCA AGCGGGTCGA GACGGCGGGC GGCGAGGTCA TCATGACTCC GATGGACGTC     1560

CTCGGCCTC                                                            1569
```

(2) INFORMATION FOR SEQ ID NO:4:

(i) SEQUENCE CHARACTERISTICS:
        (A) LENGTH: 1401 base pairs
        (B) TYPE: nucleic acid
        (C) STRANDEDNESS: double
        (D) TOPOLOGY: linear (ii) MOLECULE TYPE: DNA (vi) ORIGINAL SOURCE:
        (A) ORGANISM: Streptomyces peucetius (ix) FEATURE:
        (A) NAME/KEY: CDS
        (B) LOCATION:190..1398

(xi) SEQUENCE DESCRIPTION: SEQ ID NO: 4:

```
AGTACTGCCA GATCGAGCGG CTGGGGAACC TGGCCGCGCT GCCGGGGTGC GACGGCTTCC       60

AGGTCGCCTG CTTCCCCGTG AAGATCACCG GCGGGGGGGC CGGCTGGACC CGCGCGGTCG      120

CCTTCGTCGA CGAATGAACG TTCCGGGCGG TGGCCCCGGA CCGGCGGCCA CTCAGCATCG      180

AGAGGGATC ATG GAG CCG AAC GAA TCG ACA TGT CGT ATC TGC GGT GGC          228
          Met Glu Pro Asn Glu Ser Thr Cys Arg Ile Cys Gly Gly
            1               5                  10

CGA GTA CGG GAG TTC TTC GAC TTC GGC CGC CAG CCG CTG TCC GAC TAC        276
Arg Val Arg Glu Phe Phe Asp Phe Gly Arg Gln Pro Leu Ser Asp Tyr
       15                  20                  25
```

```
TTC CCG TCG GAG GAG GAG CTC GAC AAC GAG TTC TTC TTC CGG CTC GCG       324
Phe Pro Ser Glu Glu Glu Leu Asp Asn Glu Phe Phe Phe Arg Leu Ala
 30              35                  40                  45

GTC GGG ATG TGC GTC ACG TGC ACC ATG GTC CAG CTG CTG GAG GAG GTG       372
Val Gly Met Cys Val Thr Cys Thr Met Val Gln Leu Leu Glu Glu Val
                 50                  55                  60

CCC AGG GAC CGC ATG TTC CGC TAC GAC TAC CCG TAC CAC TCG TCG GGG       420
Pro Arg Asp Arg Met Phe Arg Tyr Asp Tyr Pro Tyr His Ser Ser Gly
                     65                  70                  75

TCG GAG CGG ATG CGC GAG CAC TTC GCG GCG ACC GCC CGC CGG CTG ATC       468
Ser Glu Arg Met Arg Glu His Phe Ala Ala Thr Ala Arg Arg Leu Ile
                 80                  85                  90

GGC ACC GAG CTG ACC GGG CGG GAC CCG TTC TGC GTG GAG ATC GGC AGC       516
Gly Thr Glu Leu Thr Gly Arg Asp Pro Phe Cys Val Glu Ile Gly Ser
         95                 100                 105

AAC GAC GGA GTG ATG CTC CGC ACG GTG CGC GAC GCC GGT GTC CGA CAC       564
Asn Asp Gly Val Met Leu Arg Thr Val Arg Asp Ala Gly Val Arg His
110                 115                 120                 125

CTG GGC GTG GAG CCT TCC GGC GGT GTC GCC GAC GTG TCC CGG GCC GAG       612
Leu Gly Val Glu Pro Ser Gly Gly Val Ala Asp Val Ser Arg Ala Glu
                130                 135                 140

GGC ATC CAG GTG CGG ACC GCG TTC TTC GAG GAG TCC ACG GCC CGG GAG       660
Gly Ile Gln Val Arg Thr Ala Phe Phe Glu Glu Ser Thr Ala Arg Glu
            145                 150                 155

ATC GCC CAG GAA CAC GGG CCC GCG AAC GTC ATC TAC GCG GCC AAC ACG       708
Ile Ala Gln Glu His Gly Pro Ala Asn Val Ile Tyr Ala Ala Asn Thr
        160                 165                 170

ATC TGT CAT ATC CCG TAC CTC GAC TCC GTC TTC CGC GGT ATC GAC GCC       756
Ile Cys His Ile Pro Tyr Leu Asp Ser Val Phe Arg Gly Ile Asp Ala
    175                 180                 185

CTC CTC GCG CCG GAC GGC GTC TTC GTC TTC GAG GAC CCC TAC CTC GGC       804
Leu Leu Ala Pro Asp Gly Val Phe Val Phe Glu Asp Pro Tyr Leu Gly
190                 195                 200                 205

GAC ATC GTC GAG AAG AAC ACC TTC GAC CAG ATC TAC GAC GAG CAC TTC       852
Asp Ile Val Glu Lys Asn Thr Phe Asp Gln Ile Tyr Asp Glu His Phe
                210                 215                 220

TAC CTG TTC ACC GCC CGC TCG GTG AGC ACC ACC GCC CAG CAC TTC GGA       900
Tyr Leu Phe Thr Ala Arg Ser Val Ser Thr Thr Ala Gln His Phe Gly
            225                 230                 235

TTC GAA CTG GTC GAC GTG GAG CGG CTC CCG GTG CAC GGC GGC GAG GTC       948
Phe Glu Leu Val Asp Val Glu Arg Leu Pro Val His Gly Gly Glu Val
        240                 245                 250

CGC TAC ACC ATC GCC CGC GCG GGC CGG CGG CAG CCG AGC CCC CGG GTC       996
Arg Tyr Thr Ile Ala Arg Ala Gly Arg Arg Gln Pro Ser Pro Arg Val
    255                 260                 265

GGC GAG CTC ATC GCC GAG GAG AGC CGG CGC GGG CTC GCC GAC CTG ACG      1044
Gly Glu Leu Ile Ala Glu Glu Ser Arg Arg Gly Leu Ala Asp Leu Thr
270                 275                 280                 285

ACG CTG GAG AAG TTC GGC GCC CAG GTC AAG CGG GTC TGC TGT GAC CTG      1092
Thr Leu Glu Lys Phe Gly Ala Gln Val Lys Arg Val Cys Cys Asp Leu
                290                 295                 300

GTG GCC CGT CTG CGC GAG CTG CGC GAC CTC GGC TTC TAC GTC GTC GGG      1140
Val Ala Arg Leu Arg Glu Leu Arg Asp Leu Gly Phe Tyr Val Val Gly
            305                 310                 315

TAC GGG GCG ACC GCC AAG AGC GCC ACA GTG CTC AAC TAT GCG GGG ATC      1188
Tyr Gly Ala Thr Ala Lys Ser Ala Thr Val Leu Asn Tyr Ala Gly Ile
        320                 325                 330

GGC CCC GAT CTG CTG CCG TGC GTC TAC GAC ACC ACG CCG GCC AAG ATC      1236
Gly Pro Asp Leu Leu Pro Cys Val Tyr Asp Thr Thr Pro Ala Lys Ile
```

```
      335                 340                 345
GGC CGT CGG CTC CCC GGG TCC CAC ATC CCC ATC CGC TCC GCC GAG GAG       1284
Gly Arg Arg Leu Pro Gly Ser His Ile Pro Ile Arg Ser Ala Glu Glu
350                 355                 360                 365

TTC CGG GCC CCC TAC CCC GAC TAT GCG CTG CTC TTC GCC TGG AAC CAC       1332
Phe Arg Ala Pro Tyr Pro Asp Tyr Ala Leu Leu Phe Ala Trp Asn His
                370                 375                 380

CTA GAC GAA GTC CAG GCC CGA GAG GCG GAG TTC ACG AAG CAG GGG GGC       1380
Leu Asp Glu Val Gln Ala Arg Glu Ala Glu Phe Thr Lys Gln Gly Gly
            385                 390                 395

CGC TGG ATC CGC TCA GGG TGA                                           1401
Arg Trp Ile Arg Ser Gly
            400
```

(2) INFORMATION FOR SEQ ID NO: 5:

(i) SEQUENCE CHARACTERISTICS:
        (A) LENGTH: 403 amino acids
        (B) TYPE: amino acid
        (D) TOPOLOGY: linear (ii) MOLECULE TYPE: protein (xi) SEQUENCE DESCRIPTION: SEQ ID NO: 5:

```
Met Glu Pro Asn Glu Ser Thr Cys Arg Ile Cys Gly Gly Arg Val Arg
 1               5                  10                  15

Glu Phe Phe Asp Phe Gly Arg Gln Pro Leu Ser Asp Tyr Phe Pro Ser
            20                  25                  30

Glu Glu Glu Leu Asp Asn Glu Phe Phe Arg Leu Ala Val Gly Met
        35                  40                  45

Cys Val Thr Cys Thr Met Val Gln Leu Leu Glu Glu Val Pro Arg Asp
    50                  55                  60

Arg Met Phe Arg Tyr Asp Tyr Pro Tyr His Ser Ser Gly Ser Glu Arg
65                  70                  75                  80

Met Arg Glu His Phe Ala Ala Thr Ala Arg Arg Leu Ile Gly Thr Glu
                85                  90                  95

Leu Thr Gly Arg Asp Pro Phe Cys Val Glu Ile Gly Ser Asn Asp Gly
            100                 105                 110

Val Met Leu Arg Thr Val Arg Asp Ala Gly Val Arg His Leu Gly Val
        115                 120                 125

Glu Pro Ser Gly Gly Val Ala Asp Val Ser Arg Ala Glu Gly Ile Gln
    130                 135                 140

Val Arg Thr Ala Phe Phe Glu Glu Ser Thr Ala Arg Glu Ile Ala Gln
145                 150                 155                 160

Glu His Gly Pro Ala Asn Val Ile Tyr Ala Ala Asn Thr Ile Cys His
                165                 170                 175

Ile Pro Tyr Leu Asp Ser Val Phe Arg Gly Ile Asp Ala Leu Leu Ala
            180                 185                 190

Pro Asp Gly Val Phe Val Phe Glu Asp Pro Tyr Leu Gly Asp Ile Val
        195                 200                 205

Glu Lys Asn Thr Phe Asp Gln Ile Tyr Asp Glu His Phe Tyr Leu Phe
    210                 215                 220

Thr Ala Arg Ser Val Ser Thr Thr Ala Gln His Phe Gly Phe Glu Leu
225                 230                 235                 240

Val Asp Val Glu Arg Leu Pro Val His Gly Glu Val Arg Tyr Thr
                245                 250                 255

Ile Ala Arg Ala Gly Arg Arg Gln Pro Ser Pro Arg Val Gly Glu Leu
```

```
              260                 265                 270
Ile Ala Glu Glu Ser Arg Arg Gly Leu Ala Asp Leu Thr Thr Leu Glu
            275                 280                 285
Lys Phe Gly Ala Gln Val Lys Arg Val Cys Cys Asp Leu Val Ala Arg
        290                 295                 300
Leu Arg Glu Leu Arg Asp Leu Gly Phe Tyr Val Val Gly Tyr Gly Ala
305                 310                 315                 320
Thr Ala Lys Ser Ala Thr Val Leu Asn Tyr Ala Gly Ile Gly Pro Asp
                325                 330                 335
Leu Leu Pro Cys Val Tyr Asp Thr Thr Pro Ala Lys Ile Gly Arg Arg
            340                 345                 350
Leu Pro Gly Ser His Ile Pro Ile Arg Ser Ala Glu Glu Phe Arg Ala
        355                 360                 365
Pro Tyr Pro Asp Tyr Ala Leu Leu Phe Ala Trp Asn His Leu Asp Glu
    370                 375                 380
Val Gln Ala Arg Glu Ala Glu Phe Thr Lys Gln Gly Gly Arg Trp Ile
385                 390                 395                 400
Arg Ser Gly
```

(2) INFORMATION FOR SEQ ID NO: 6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide primer"

(xi) SEQUENCE DESCRIPTION: SEQ ID NO: 6:

CGCCAGGGTT TTCCCAGTCA CGAC                     24

(2) INFORMATION FOR SEQ ID NO: 7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide primer"

(xi) SEQUENCE DESCRIPTION: SEQ ID NO: 7:

AGCGGATAAC AATTTCACAC AGGA                     24

PROCESS FOR PREPARING DOXORUBICIN

This application is a national stage filing under 35 U.S.C. §371 of the International Application No. PCT/US98/03938, filed Mar. 5, 1998, and is also a Continuation-In-Part of U.S. application Ser. No. 08/901,306 filed Jul. 28, 1997, which has issued as U.S. Pat. No. 5,955,319, and a Continuation-In-Part of U.S. application Ser. No. 08/812,412 filed Mar. 6, 1997, which has issued as U.S. Pat. No. 5,989,869.

FIELD OF THE INVENTION

The present invention concerns a process for improving doxorubicin production by means of a recombinant strain bearing a mutation in a gene of daunorubicin metabolism.

BACKGROUND OF THE INVENTION

Anthracyclines of the daunorubicin group such as doxorubicin, carminomycin and aclacinomycin and their synthetic analogs are among the most widely employed agents in antitumoral therapy (F. Arcamone, Doxorubicin, Academic Press New York, 1981, pp. 12–25; A. Grein, Process Biochem., 16:34, 1981; T. Kaneko, Chimicaoggi May 11, 1988; C. E. Myers et al., "Biochemical mechanism of tumor cell kill" in Anthracycline and Anthracenedione-Based Anti-cancer Agents (Lown, J. W., ed.) Elsevier Amsterdam, pp. 527–569, 1988; J. W. Lown, Pharmac. Ther. 60:185–214, 1993). Anthracyclines of the daunorubicin group are naturally occurring compounds produced by various Streptomyces species and by *Actinomyces carminata*. Doxorubicin is mainly produced by strains of *Streptomyces peucetius* while daunorubicin is produced by many other Actinomycetes. In particular daunorubicin and doxorubicin are synthesized in *S. peucetius* ATCC 29050 and 27952 from malonic acid, propionic acid and glucose by the pathway summarized in Grein (Advan. Applied Microbiol. 32:203, 1987) and in Eckart and Wagner (J. Basic Microbiol. 28:137, 1988). Aklavinone (11-deoxy-ε-rhodomycinone), ε-rhodomycinone and carminomycin are established intermediates in this process. The final step in this pathway involves the hydroxylation of daunorubicin to doxorubicin by the DoxA enzyme ({U.S. Ser. No. 08/396,218, WO96/27014}; M. L. Dickens and W. R. Strohl, J. Bacteriol. 178:3389 (1996)), which is reported to occur only in *S. peucetius*.

13-Dihydrodaunorubicin may be an intermediate in the conversion of ε-rhodomycinone to daunorubicin via rhodomycin D (FIG. 1) according to Dickens et al. (J. Bacteriol. 179:2641 (1997)). Daunorubicin is bioconverted to (13S)-13-dihydrodaunorubicin when added to cultures of *S. peucetius* and some other Streptomycetes (N. Crespi-Perellino et al., Experientia, 38:1455, 1982; T. Oki et al., J. Antibiotics, 34:1229, 1981; G. Cassinelli et al., Gazz. Chim. Ital. 114:185,1984). It is not known whether the 13-dihydrodaunorubicin that may be an intermediate in daunorubicin and doxorubicin production in *S. peucetius* is identical to the (13S)-13-dihydrodaunorubicin formed by this bioconversion. Since these two compounds can differ in their C-13 stereochemistry, one diastereomer of 13-dihydrodaunorubicin might be a substrate for DoxA and the other one would not. In the latter case, C-13 reduction of daunorubicin would block its further oxidation to doxorubicin.

Several genes for daunorubicin and doxorubicin biosynthesis and resistance have been isolated from *S. peucetius* 29050 and 27952 by cloning experiments. The *S. peucetius* dnrU gene identified herein is a homolog of the Streptomyces sp. strain C5 gene ORF1 (syn. dauU) described by Dickens and Strohl (J. Bacteriol. 178:3389 (1996)). Since the predicted protein products of the dnrU and dauU genes resemble enzymes known to reduce ketone groups, the dnrU and dauU proteins may catalyze the reduction of daunorubicin, formed in vivo or added to cultures exogenously, to 13-dihydrodaunorubicin.

Daunorubicin is known to be converted to 4'-O-glycosides called baumycins in Streptomyces species (Y. Takahashi, H. Naganawa. T. Takeuchi, H. Umezawa, T. Komiyama, T. Oki and T. Inui. J. Antibiot. 30:622, 1977) thus decreasing also the amount of doxorubicin potentially obtainable through oxidation of daunorubicin. For recovering daunorubicin at the end of fermentation, baumycins are converted to daunorubicin by acid hydrolysis. However this process presents certain drawbacks in that the amount of doxorubicin thus produced is low and the process is complicated by the acid hydrolysis step. The present invention solves this problem by providing a mutated Streptomyces strain in which one of the genes responsible for the conversion of daunorubicin to baumycins has been insertionally inactivated.

SUMMARY OF THE INVENTION

The present invention concerns a process for preparing doxorubicin by means of a bacteria recombinant strain bearing at least one mutation and preferably two mutations blocking the function of at least one gene of daunorubicin metabolism. The inactivating mutations increase daunorubicin and doxorubicin production levels and cause the disappearance of baumycin-like products resulting in daunorubicin and doxorubicin secretion directly into the culture medium. Consequently, there is no need to acidify the cultures at the end of fermentation. The relative amounts of 6-rhodomycinone and 13-dihydrodaunorubicin may also be altered, as an incidental consequence of the mutation. Preferably the bacterium is a strain of Streptomyces sp. producing daunorubicin and doxorubicin, having at least one mutation blocking the function of at least one gene of daunorubicin metabolism.

One of the inactivated genes is preferably in the DNA fragment having the configuration of restriction sites shown in FIG. 5 or in a fragment derived therefrom containing a gene, dnrX, encoding a protein involved in the metabolism of daunorubicin to acid-sensitive, baumycin-like compounds.

The second inactivated gene is preferably comprised in the DNA fragment having the configuration of restriction sites shown in FIG. 3 or in a fragment derived therefrom containing a gene, dnrU, coding for a protein involved in the metabolism of daunorubicin.

The present invention provides a mutant strain of *S. peucetius*, obtained from *S. peucetius* ATCC 29050, having a mutation blocking the function of the dnrU gene. This mutation greatly increases the doxorubicin production level relative to the amount of daunorubicin, and by coincidence may also increase the amount of ε-rhodomycinone.

The present invention also provides a mutant strain of *S. peucetius*, obtained from *S. peucetius* ATCC 29050, having a mutation inactivating the function of the dnrX gene.

The present invention also provides a mutant strain of *S. Peucetius*, obtained from *S. peucetius* ATCC 29050, having a mutation inactivating the function of both the dnrX and dnrU genes.

Genes for daunorubicin and doxorubicin biosynthesis and resistance have been obtained from *S. peucetius* 29050 and S. peucetius 27952 by cloning experiments as described in Stutzman-Engwall and Hutchinson (Proc. Natl. Acad. Sci. USA, 86: 3135 (1988)) and Otten et al., (J. Bacteriol. 172: 3427 (1990)).

The dnrU mutant can be obtained by disrupting the dnrU gene, obtained from the *S. peucetius* 29050 anthracycline production genes described by Stutzman-Engwall and Hutchinson (Proc. Natl. Acad. Sci. USA, 86: 3135 (1988)) and Otten et al. (J. Bacteriol. 172: 3427 (1990)), by insertion of the neomycin/kanamycin resistance gene (aphII) into the BalI restriction site located at the beginning of dnrU. This disrupted dnrU::aphII gene is used to replace the normal dnrU gene in the 29050 strain.

The dnrX mutant was obtained by disrupting the dnrX gene of the anthracycline biosynthetic gene cluster by insertion of the neomycin/kanamycin resistance gene (aphII) in the NcoI restriction site of dnrX.

BRIEF DESCRIPTION OF THE DRAWINGS

FIG. 2A and 2B show the DNA and deduced protein sequences of the dnrU gene and part of the dnrV gene. SEQ ID 1 is a schematic illustration of the dnrU DNA nucleotide sequence. Said DNA corresponds to that encoding a protein for daunorubicin metabolism. The sequence covers the region between the SstI and the AatII restriction sites and shows the coding strand in the 5' to 3' direction. The derived amino acid sequence of the translated open reading frame encoding a protein required for daunorubicin metabolism is shown below the nucleotide sequence of the dnrU gene as SEQ ID 2.

FIG. 4 is the structure of KC515 and phWHM295 containing the disrupted copy the dnrU gene. ΔattP and cos indicate the relative locations of the deletion in the phage attachment site and the cohesive end of KC515, respectively; tsr, vph and aphII are the thiostrepton, viomycin and neomycin resistance genes, respectively. (Restriction site abbreviations: Ba, BamHI; Bg, Bg/II; Hp, HpaII; No, NotI; Nr, NruI; Ps PstI; Pv, PvuII; Ss, SstI and Xh, XhoI).

FIG. 5 is a restriction map analysis of the DNA of the invention. Said DNA is a BamHI fragment of 3.3 kb, containing the dnrX gene, obtained from the cosmid clone pWHM335 described in Stutzman-Engwall and Hutchinson (Proc. Natl. Acad. Sci. U.S.A. 86: 3135 (1988)) and Otten et al., (J. Bacteriol. 172: 3427 (1990)). The fragment was inserted into the unique BamHI restriction site of the polylinker region of plasmid pUC19 (Yanish-Perron C. et al., Gene 33:103–119 (1985)). The map shown in FIG. 5 does not necessarily provide an exhaustive listing of all restriction sites present in the DNA fragment. However, the reported sites are sufficient for an unambiguous recognition of the DNA segment. [Restriction site abbreviations: Ba, BamHI; Nc, NcoI; Sc, ScaI; Xm, XmaI; Aw, AIwNI; Bg, BgIII; Pv, PvuI.]

Figure 1:
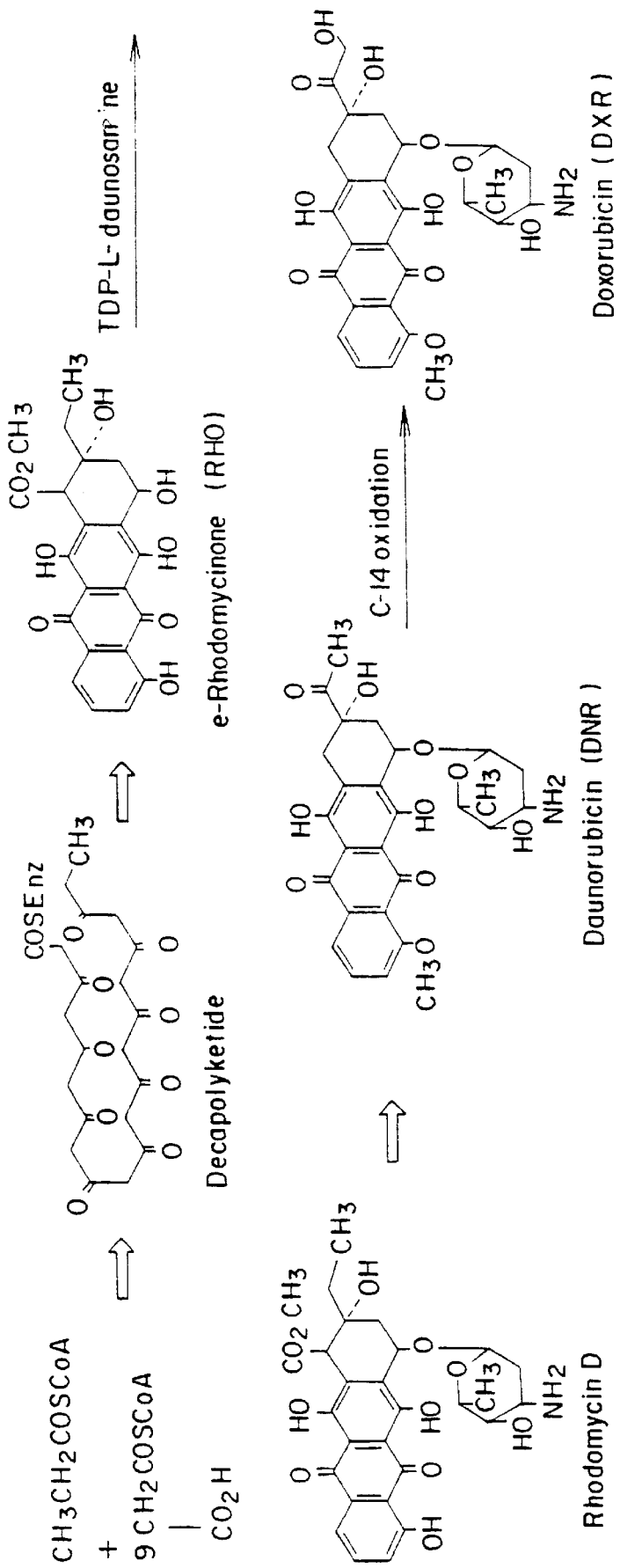
FIG. 1 is a summary of the biosynthetic pathway to daunorubicin and doxorubicin in *S. peucetius*.

SEQ ID NO:4 sets forth the dnrX DNA nucleotide sequence. Said DNA corresponds to that encoding a protein required for daunorubicin metabolism. The sequence covers the region between the ScaI and the BamHI restriction sites and shows the coding strand in the 5' to 3' direction. The derived amino acid sequence of the translated open reading frame encoding a protein required for daunorubicin glycosylation is shown under (SEQ ID NO:5).

DESCRIPTION OF THE INVENTION

The present invention provides a bacteria recombinant strain bearing a mutation inactivating the function of the daunorubicin metabolism gene dnrU and/or dnrX. The bacterial strain may be one that is daunorubicin- or doxorubicin-sensitive, i.e. cannot grow in the presence of a certain amount of daunorubicin or doxorubicin, or that is daunorubicin- or doxorubicin-resistant. Strains belonging to the Streptomyces genus constitute a preferred embodiment of the invention; a *Streptomyces peucetius* strain constitutes a particularly preferred embodiment of the invention. Most preferred are the *S. peucetius* strains WMH1658, WMH1654 and WMH 1662. The strain WMH1658 was deposited at the American Type Culture Collection, Rockville, Md., USA, under the accession number ATCC 55994. The strain WMH1654 was deposited at the American Type Culture Collection, Rockville, Md., USA, under the accession number ATCC 55936. The strain WMH1662 was deposited at the American Type Culture Collection, Rockville, Md., USA, under the accession number ATCC 202051.

The WMH1658 strain was obtained from *S. peucetius* ATCC 29050 strain by replacing the dnrU gene with a mutated dnrU gene into which the neomycin/kanamycin resistance gene (aphII) from the pFDNEO-S plasmid described by F. Danis and R. Brzezinski, (FEMS Microbiology Letters 81:261 (1991 ) was inserted. The aphII gene was inserted into the BalI restriction site located at the beginning of dnrU to disrupt the function of dnrU, as better explained in Example 1.

The WMH1654 strain was obtained from the *S. peucetius* ATCC 29050 strain by replacing the dnrX gene with a mutated dnrX gene insertionally inactivated by introduction of the neomycin/kanamycin resistance gene (aphII) from pFDNEO-S plasmid described by F. Danis and R. Brzezinski, (FEMS Microbiology Letters 81:261–264 (1991)). The aphII gene was inserted at the NcoI site of dnrX to disrupt its function, as better explained in Example 4.

The WMH1662 strain was obtained from the *S. peucetius* ATCC 29050 strain by replacing the dnrX and dnrU genes with mutated dnrX and dnrU genes insertionally inactivated by introduction of the neomycin/kanamycin resistance gene (aphII) from pFDNEO-S plasmid described by F. Danis and R. Brzezinski, (FEMS Microbiology Letters 81:261–264 (1991)). The aphII gene was inserted at the NcoI site of dnrX and into the BalI site of dnrU to disrupt their function, as better explained in Example 7.

The expert in the art will recognize that any other technique to inactivate the gene can be suitably employed in the present invention.

The bacterial recombinant strain may be any other microorganism transformed with plasmids or transfected with phage DNA containing an anthracycline gene cluster able to produce daunorubicin and/or doxorubicin and/or baumycins.

In another aspect, the present invention provides a process for preparing doxorubicin, which process comprises:
(i) culturing a bacterial recombinant strain of the invention, and
(ii) isolating doxorubicin and/or daunorubicin from the culture.

In this process the bacterial recombinant strain may be cultured at from 20 to 40° C, preferably from 26 to 37° C. The culture is preferably carried out with agitation. In order to obtain the bacterial recombinant strain of the invention, the dnrU and dnrX genes were isolated from clones described in Stutzman-Engwall and Hutchinson, (Proc. Acad. Sci. USA 86:3135 (1989) and Otten et al., (J. Bacteriol. 172:3427 (1990).

Figure 2B:
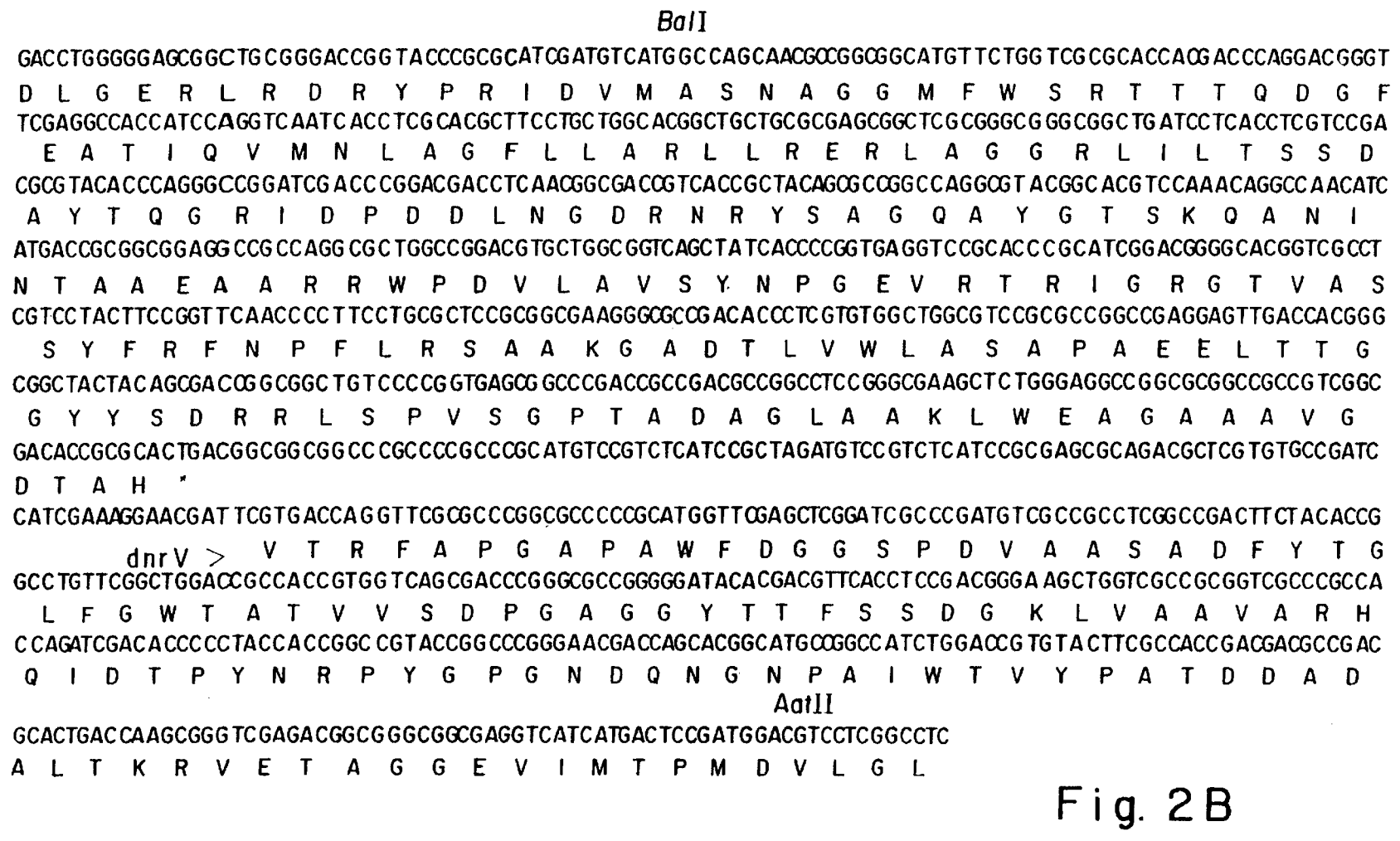

The dnrU gene is contained in a 4.8-kb BamHI-NruI fragment obtained from the cosmid clone pWHM335 described in Stutzman-Engwall and Hutchinson (Proc. Natl. Acad. Sci. USA, 86: 3135 (1988)) and Often et al. (J. Bacteriol. 172: 3427 (1990)). This 4.8 kb BamHI-NruI fragment can be further digested to give the 1.55 kb SstI-AatI fragment whose sequence (SEQ ID NO:3) is shown in FIG. 2. The 1.55 kb SstI-AatI fragment includes the dnrU gene and part of the dnrV gene.

The dnrX gene is contained in a 3.3 kb DNA fragment obtained by digestion of the clone pWHM335 with the restriction endonuclease BamHI.

The dnrU gene consists essentially of the sequence of SEQ ID NO 1, which sequence will be referred to as the "dnrU" sequence. The deduced amino acid sequence of the daunorubicin and doxorubicin metabolism protein encoded by SEQ ID NO 1 is shown in SEQ ID NO 2. The isolated dnrU gene was subsequently subcloned into an appropriate DNA cloning vector.

The dnrX gene consists essentially of the sequence of SEQ. ID NO. 4, which sequence will be referred to as the "dnrX" sequence. The deduced amino acid sequence of the daunorubicin and doxorubicin metabolism protein encoded by SEQ. ID NO.4 is shown in SEQ. ID NO. 5. The isolated dnrX gene was subsequently subcloned into an appropriate DNA cloning vector.

Any autonomously replicating and/or integrating agent comprising a DNA molecule to which one or more additional DNA segments can be added may be used. Typically, however, the vector is a plasmid. Preferred plasmids are pUC19 (Yanish-Perron et al., Gene 33: 103 (1985)) and pWHM3 (Vara et al., J. Bacteriol. 171:5872 (1989)). Any suitable technique may be used to insert the DNA into the vector. Insertion can be achieved by ligating the DNA into a linearized vector at an appropriate restriction site. For this, direct combination of sticky or blunt ends, homopolymer tailing, or the use of a linker or adapter molecule may be employed. The recombinant plasmid is then digested with a suitable restriction enzyme and ligated with the aphII gene. This construction is transferred into a suitable vector for homologous integration. Among the possible vectors that can be used, KC515 (Hopwood et al., Genetic Manipulation of Streptomyces. A Laboratory Manual, John Innes Foundation, Norwich, UK, 1985)) or pKC1 139 (M. Bierman et al., Gene 1 16:43–49 (1992)) are preferred. KC515 is a derivative of $\phi$C31 and can only transduce a host to antibiotic resistance if the vector carries a segment of homologous DNA, and pKC1 139 is an E. coli-Streptomyces shuttle vector that contains a temperature-sensitive replicon that functions well at temperature below 34° C. and bears the apramycin resistance gene. The recombinant vector thus obtained is used to transform, typically with KC515 by transduction with infective phage particles or with pKC1139 by protoplast transformation, an appropriate Streptomyces strain; the final step in this inactivation protocol is the isolation of kanamycin resistant transformant in which the recombinant plasmid has recombined with the dnrU and/or dnrX genes and inactivated it (see Examples 1, 4 and 7).

On the basis of the information provided herein, the expert in the art can easily obtain the 1.55 kb SstI-AatII and 3.3 kb BamHI DNA fragments by:
a) preparing a library of the genomic DNA of S. peucetius 29050 or a strain derived therefrom:
b) screening the library for clones positive to a labelled probe, of at least 24 nucleotides, synthesized according to the sequence of SEQ ID NO: 1 or SEQ ID NO: 4;
c) obtaining an insert DNA, from a recombinant vector, that forms part of the library and that has been screened as positive for the ability to metabolize daunorubicin to doxorubicin in the S. peucetius dnrU mutant or the ability to convert daunorubicin into the acid-sensitive metabolite form in the S. peucetius dnrX mutant.

To obtain the DNA fragment, the library may be prepared in step a) by partially digesting the genomic DNA of S. peucetius 29050 or a strain derived therefrom; or by screening a library of Streptomyces genomic DNA that has been enriched for the cluster of daunorubicin and doxorubicin biosynthesis genes. Generally the restriction enzyme MboI is preferably used for genomic DNA, but for the libraries containing the cluster of daunorubicin biosynthesis genes, the restriction enzymes BamHI is preferred. The DNA fragments thus obtained can be size fractionated; fragments from 1 to 7 kb in size are preferred for libraries containing the cluster of daunorubicin and doxorubicin biosynthesis genes. These fragments are ligated into a linearized vector such as pWHM3 or pKC505 ((M. A.Richardson et al, Gene 61:231 (1987)). E. coli DH5α and DH1 are respectively transformed or transfected with the ligation mixtures. in step b) the colonies obtained by the transformations are transferred to nylon membranes and screened by colony hybridization for plasmids or cosmids which hybridize to the labelled probe, of at least 24 nucleotides, synthesized according to the sequence of SEQ ID No:1 and/or SEQ ID NO:4.

In step c) plasmid DNA from the clones which hybridized to the probe is isolated and used to transform protoplasts of host cells. The hosts may be microorganisms that produce less doxorubicin than daunorubicin or microorganisms that do not produce acid-sensitive, baumycin-like compounds. The S. peucetius dnrU mutant strain (ATCC 55994) that produces more doxorubicin than daunorubicin and, coincidentally, more ε-rhodomycinone than the 29050 strain, and the S. peucetius dnrX mutant strain (ATCC 55936) that does not produce acid-sensitive, baumycin-like compounds represent particularly suitable hosts.

Clones containing DNA fragments which include the 1.55 kb SstI-AatII DNA fragment (SEQ ID NO:3) of the invention, when introduced into the S. peucetius dnrU mutant strain (ATCC 55994), are recognized by the appearance in fermentation cultures of decreased levels of doxorubicin relative to daunorubicin and, coincidentally, ε-rhodomycinone.

Clones containing DNA fragments which include the 3.3 kb BamHI DNA fragment of the invention are recognized by the appearance in non-acidified fermentation cultures of acid-sensitive, baumycin-like compounds.

MATERIALS AND METHODS

Bacterial Strains and Plasmids

E. coli strain DH5α (Sambrook et al., Molecular cloning. A laboratory Manual, 2nd ed. Cold Spring Harbor Press, Cold Spring Harbor, N.Y., 1989), which is sensitive to ampicillin, is used for subcloning DNA fragments. S. peucetius ATCC 29050 and a S. peucetius dnrU mutant that produces more doxorubicin than daunorubicin and, coincidentally, more ε-rhodomycinone than the 29050 strain are used for disruption and expression, respectively, of the dnrU gene. Streptomyces lividans TK24 (D. A. Hopwood et al., J. Gen. Microbiol. 129:2257 (1983)) and S. lividans TK24(φC31) lysogen are used in transfection experiments (Hopwood et al., Genetic Manipulation of Streptomyces. A Laboratory Manual, John Innes Foundation, Norwich, UK, 1985) and for screening of phage carrying a cloned chromosomal DNA fragment (N. D. Lomovskaya et al., J. Bacteriol. 178:3238 (1996) or N. D. Lomovskaya et al. Microbiology 143:875 (1997)). S. peucetius dnrX mutant that does not produce acid-sensitive daunorubicin metabolites is used for expression of the dnrX gene. The vector for homologous integration is pKC1139 (M. Bierman et al., Gene 116:43–49 (1992)), a shuttle E. coli-Streptomyces vector.

The plasmid cloning vectors are pUC18/19 ((Yanish-Perron et al., Gene 33:103 (1985)), pSE380 (Invitrogen Corp.), pSP72 (Promega), and pWHM3 (Vara et al., J. Bacteriol. 171:5872 (1989)). The integrative vector is KC515, a derivative of phage φC31 (Hopwood et al., Genetic Manipulation of Streptomyces. A Laboratory Manual, John Innes Foundation, Norwich, UK, 1985). The pFDNEO-S plasmid described by F. Danis and R. Brzezinski, (FEMS Microbiology Letters 81:261–264 (1991)) is used to get the neomycin/kanamycin aphII resistance gene.

Media and Buffer:

E. coli strain DH5α is maintained on LB agar (Sambrook et al., Molecular cloning. A laboratory Manual, 2nd ed. Cold Spring Harbor Press, Cold Spring Harbor, N.Y., 1989). When selecting for transformants, ampicillin and/or apramycin are added at a concentration of 100 micrograms/ml and/or 50 micrograms/ml respectively. S. peucetius 29050, S. peucetius dnrX::aphII and dnrU::aphII strains are maintained on ISP4 agar (Difco Laboratories, Detroit, Mich.) for the preparation of spores and on R2YE agar (Hopwood et al., Genetic Manipulation of Streptomyces. A Laboratory Manual, John Innes Foundation, Norwich, UK, 1985) for regeneration of protoplasts. When selecting for transformants the plates are overlayed with 20 micrograms/ml thiostrepton and/or soft agar containing 350 micrograms/ml apramycin corresponding to a final concentration in the plates of 40 micrograms/ml apramycin. R2YE agar without sucrose is used when S. peucetius 29050 is infected with phage phWHM295.

Subcloning DNA Fragments:

DNA samples are digested with appropriate restriction enzymes and separated on agarose gel by standard methods (Sambrook et al., Molecular cloning. A Laboratory Manual, 2nd ed. Cold Spring Harbor Press, Cold Spring Harbor, N.Y., 1989). Agarose slices containing DNA fragments of interest are excised from a gel and the DNA is isolated from these slices using the GENECLEAN device (Bio101, La Jolla, Calif.) or an equivalent. The isolated DNA fragments are subcloned using standard techniques (Sambrook et al., Molecular cloning. A Laboratory Manual, 2nd ed. Cold Spring Harbor Press, Cold Spring Harbor, N.Y., 1989) into E. coli for routine manipulations, including DNA sequencing, and E. coli-Streptomyces shuttle vectors or Streptomyces vectors for expression experiments and fermentations.

DNA Sequencing of the dnrX Gene.

In order to sequence the fragment containing the gene of interest, the following synthetic oligonucleotide primers for pUC19 have been synthesized:

pU C Sequencing Primer (−47) 24-mer:
5'd(CGCCAGGGTTTTCCCAGTCACGAC)3' (SEQ ID NO:6);

pUC Reverse Sequencing (−48) 24-mer:
5'd(AGCGGATAACAATTTCACACAGGA)3' (SEQ ID NO:7).

The sequence determination has been performed simultaneously on both strands.

Transformation of E. coli and Streptomyces Species:

Competent cells of E. coli are prepared by the calcium chloride method (Sambrook et al., Molecular cloning. A Laboratory Manual, 2nd ed. Cold Spring Harbor Press, Cold Spring Harbor, N.Y., 1989) and transformed by standard techniques (Sambrook et al., Molecular cloning. A Laboratory Manual, 2nd ed. Cold Spring Harbor Press, Cold Spring Harbor, N.Y., 1989). S. peucetius 29050, S. peucetius dnrX::aphII mycelium, and/or S. peucetius dnrU::aphII mycelium is grown in R2YE medium (Hopwood et al., Genetic Manipulation of Streptomyces. A Laboratory Manual, John Innes Foundation, Norwich, UK, 1985) and harvested after 24 or 48 hours. The mycelial pellet is washed twice with 10.3% (wt/vol) sucrose solution and used to prepare protoplasts according to the method outlined in the Hopwood manual (Hopwood et al., Genetic Manipulation of Streptomyces. A Laboratory Manual, John Innes Foundation, Norwich, UK, 1985). The protoplast pellet is suspended in about 300 microlitres of P buffer (Hopwood et al., Genetic Manipulation of Streptomyces. A Laboratory Manual, John Innes Foundation, Norwich, UK, 1985) and a 50 microliter aliquot of this suspension is used for each transformation. Protoplasts are transformed with plasmid DNA according to the small scale transformation method of Hopwood et al. (Genetic Manipulation of Streptomyces. A Laboratory Manual, John Innes Foundation, Norwich, UK, 1985), Stutzman-Engwall and Hutchinson (Proc. Natl. Acad. Sci. USA, 86: 3135 (1988) or Otten et al. (J. Bacteriol. 172: 3427 (1990)). After 17 hr of regeneration on R2YE medium at 30° C., the plates are overlayed with 20 micrograms/ml of thiostrepton and/or 40 micrograms/ml of apramycin and allowed to grow at 30° C until sporulated.

Doxorubicin and Daunorubicin Production:

An S. peucetius dnrX:: aphII mutant strain, S. peucetius dnrU::aphII mutant strain or S. peucetius dnrU::aphII, dnrX:: aphII mutant strain is inoculated into 25 ml of liquid R2YE medium with 40 micrograms/ml of kanamycin sulfate in a 300 ml flask and incubated at 30° C. and 300 rpm on a rotary shaker. After 2 days of growth 2.5 ml of this culture are transferred to 25 ml of APM production medium: ((g/l) glucose (60), yeast extract (8), malt extract (20), NaCI (2), 3-(morpholino)propanesulfonic acid (MOPS sodium salt) (15), $MgSO_4 \cdot 7H_2O$ (0.2), $FeSO_4 \cdot 7H_2O$ (0.01), $ZnSO_4 \cdot 7H_2O$ (0.01). Forty (40) micrograms of kanamycin are added to the S. peucetius dnrU::aphII and dnrX::aphII culture. The cultures are incubated in a 300 ml flask at 30° C. and 300 rpm on a rotary shaker for 96–120 hrs. The cultures are acidified with 250 mg oxalic acid and incubated at 30° C. over night and then extracted with an equal volume of acetonitrile:methanol (1:1) at 30° C. and 300 rpm for 2 hr. The extract is filtered and the filtrate is analyzed by reversed-phase high pressure liquid chromatography (RP-HPLC). RP-HPLC is performed by using a Vydac C18 column (4.6×250 mm; 5 micrometers particle size) at a flow rate of 0.385 ml/min. Mobile phase is 0.2% trifluoroacetic acid (TFA, from Pierce Chemical Co.) in H2O and mobile phase B is 0.078% TFA in acetonitrile (from J: T: Baker Chemical Co.). Elution is performed with a linear gradient from 20 to 60% phase B in phase A in 33 minutes and monitored with a diode array detector set at 488 nm (bandwidth 12 micrometers). ε-rhodomycinone, daunorubicin and doxorubicin (10 micrograms/ml in methanol) are used as external standards to quantitate the amount of these metabolites isolated from the cultures.

EXAMPLES

Example 1

Figure 3:
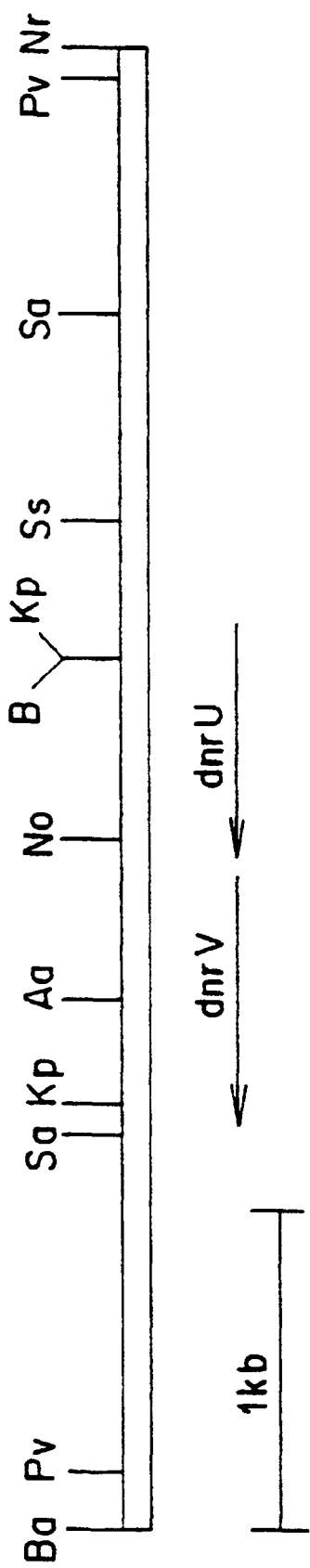
FIG. 3 is a restriction map analysis of the DNA of the invention. Said DNA is a 4.8-kb BamHI-NruI fragment containing dnrU and dnrV, subcloned from the cosmid clone pWHM335 described in Stutzman-Engwall and Hutchinson, (Proc. Natl. Acad. Sci. USA, 86:3135 (1988)) and Otten et al. (J. Bacteriol. 172: 3427 (1990)). The location and direction of transcription of the two genes are indicated by arrows. The fragment was inserted into the unique BamHI and NruI restriction sites of the polylinker region of plasmid pSE380 (Invitrogen Corp.). The map shown in FIG. 3 does not necessarily provide an exhaustive listing of all restriction sites present in the DNA fragment. However, the reported sites are sufficient for an unambiguous recognition of the DNA segment. (Restriction site abbreviations: Ba, BamHI; Sa, SalI, Kp, KpnI; No, NotI; B, BalI, Nr, NruI; Aa, AatII, Ss, SStI and Pv, PvuII).

Disruption of dnrU:

pWHM555 is constructed by subcloning the 6.0-kb BamHI fragment containing the dnrU and dnrv genes from the pWHM335 cosmid clone described by Stutzman-Engwall and Hutchinson (Proc. Acad. Sci. USA 86:3135 (1988)) and Otten et al. (J. Bacteriol. 172:3427 (1990)) in the pUC18 plasmid vector. pWHM289 is constructed by subcloning the 4.8-kb BamHI-NruI fragment containing the dnrU and dnrV genes from pWHM555 in the pSE380 vector, from which a 4.8-kb BamHI-XhoI fragment was cloned into the pSP72 vector to create pWHM290. Then the aphII gene, obtained as a 1.0 kb SalI fragment from pFDNeoS, was inserted into the BalI site located in the beginning of the structural part of dnrU to create pWHM293. A 4.0-kb AatII-XhoI fragment containing the aphII gene was cloned blunt-ended from pWHM293 into the PvuII site of pSP72 to create pWHM294, from which a 4.0-kb BamHI-XhoI fragment containing the disrupted copy of dnrU was cloned into the KC515 phage vector to create phWHM295 (FIG. 3).

Cloning of the dnrU Gene:

Cloning of S. peucetius 29050 DNA fragments into the phage integrative vector KC515 and screening of the phage carrying a disrupted copy of the dnrU gene are performed as described by Lomovskaya et al. (J. Bacteriol. 178:3238 (1996) or Microbiology 143:875 (1997)). The phage plaques obtained after transfection of S. lividans TK24 protoplasts are screened by selection for neomycin resistance with neomycin (10 micrograms/ml) added to R2YE growth medium. The presence or absence of the neomycin (aphII) and viomycin (vph) resistance genes in the phage vector is tested by adding neomycin (10 microgram/ml) and viomycin (200 microgram/ml) to R2YE medium. In this way the phage phWHM295 is characterized as containing aphII and vph resistance genes. The presence of the cloned DNA containing the disrupted dnrU::aphII gene was confirmed by restriction endonuclease digestion analysis.

S. peucetius 29050 is infected with phWHM295 (5×10$^7$ spores and 1 to 2×10$^8$ phage). After 16 h the plates are overlaid with an aqueous neomycin solution to give a final concentration of 10 microgram/ml, then after further growth for 6 d until sporulation, the plates are replica-plated on minimal medium (Hopwood et al., Genetic Manipulation of Streptomyces. A Laboratory Manual, John Innes Foundation, Norwich, UK, 1985) containing neomycin (10 micrograms/ml). Primary neomycin-resistant clones are isolated and their phenotype is determined after a second round of single colony isolation. Selection for gene replacement is carried out on minimal medium with neomycin (10 micrograms/ml) and viomycin (30 micrograms/ml). In this way, clones are obtained that are resistant to neomycin and sensitive to viomycin. Two colonies with the neomycin-resistance, viomycin-sensitive phenotype are examined by Southern analysis to verify the disruption of the dnrU gene. Chromosomal DNA from the 29050 strain and the WHM1658 dnrU mutant strain are digested with BamHI and probed with the 1.1-kb PstI-BamHI fragment of pFDNeoS containing the aphII gene. The probe hybridizes to a 7.0-kb BamHI fragment for the dnrU mutant, which is consistent with the insertion of the aphII gene in the dnrU gene.

Example 2

Enhanced ε-rhodomycinone and Doxorubicin Production in the Fermentation Broth of the WHM1658 dnrU::aphII mutant:

The dnrU::aphII mutant is grown for 10 days at 30° C. on slants of ISP4 agar medium (Difco) supplemented with 40 micrograms of kanamycin sulfate. The spores of this culture are collected and suspended in 300 ml Erlenmeyer flasks containing 25 ml of R2YE liquid medium containing 40 micrograms of kanamycin sulfate and the flasks are shaken for 2 days at 30° C. on a rotary shaker running at 300 rpm in a 5 cm diameter circle. A 2.5 ml portion of this culture is used to inoculate 25 ml of APM medium containing 40 micrograms of kanamycin sulfate in 300 ml Erlenmeyer flasks. The flasks are incubated at 30° C for 96 hr under the same conditions described for the seed cultures. The metabolites are extracted from the cultures according to the methods described in the Materials and Methods section. The production values are indicated in Table 1.

TABLE 1

Amount (micrograms/ml) of ε-rhodomycinone, daunorubicin and doxorubicin produced by the S. peucetius ATCC 29050 and WMH1658 dnrU::aphII strains in the APM medium at 96 h.

| Strain | ε-rhodomy-cinone | doxorubicin | daunorubicin | doxo/dauno ratio |
|---|---|---|---|---|
| 290950 | 11.6 | 6.6 | 10.1 | 0.65 |
| WMH1658 | 39.4 | 31.7 | 8.9 | 3.56 |

Example 3

Complementation of the dnrU::aphII Mutation with the dnrU and dnrU+dnrV Genes:

To confirm that the high production value of ε-rhodomycinone and doxorubicin in the fermentation broth of the dnrU::aphII mutant is due to dnrU disruption, the WMH1658 dnrU mutant is transformed separately with pWHM299 and pWHM345. These two plasmids are made as follows. A 1.55-kb AatII/-SstI fragment (SEQ ID NO:3) from pWHM555 containing the dnrU gene is cloned into pSE380 to create pWHM298. A 1.55-kb EcoRI-HindIII fragment from pWHM298 is cloned into pWHM3 to create pWHM299. A 3.1-kb PvuII-SstI fragment from pWHM555 containing the dnrU and dnrV genes is cloned into pSP72 to create pWHM343. A 3.1-kb EcoRI-XhoI fragment from pWHM343 is cloned into pSE380 to create pWHM344. A 3.1-kb EcoRI-HindIII fragment from pWHM344 is cloned into pWHM3 to create pWHM345. pWHM299 and pWHM345 are introduced separately into the S. peucetius WMH1658 dnrU mutant by the protoplast-mediated transformation method described above, using thiostrepton (20 micrograms/ml) for selection of the transformants. S. peucetius WMH1658 transformants are verified by reisolation of pWHM3, pWHM299 or pWHM345 according to the plasmid isolation protocol described by Hopwood et al. (Genetic Manipulation of Streptomyces. A Laboratory Manual, John Innes Foundation, Norwich, UK, 1985) and analysis of the DNA of these plasmids by restriction endonuclease digestion according to standard protocols (Sambrook et al., Molecular cloning. A Laboratory Manual, 2nd ed. Cold Spring Harbor Press, Cold Spring Harbor, N.Y., 1989). Transformants are grown in the APM medium in the presence of thiostrepton (10 micrograms/ml) and culture extracts are checked for production of ε-rhodomycinone, daunorubicin and doxorubicin production according to the procedure described above. HPLC analysis shows a decrease in the amount of ε-rhodomycinone and doxorubicin produced by the WMH1658(pWHM299) recombinant strain containing the dnrU gene and the WMH1658(pWHM345) recombinant strain containing the dnrU and dnrv genes, compared with the amounts of these metabolites produced by the WMH1658(pWHM3) transformant (typical values are shown in Table 2). As can be seen from Table 2, the complementation experiment with plasmid pWHM345 resulted in a complete restoration of doxorubicin production level. This result is not unexpected since, as already described in Solari et al., *Cloning and Expression of Daunorubicin C-14 Hydroxylase Gene from a Streptomyces peucetius Mutant*, the Sixth Conference on the Genetics and Molecular Biology of Industrial Microorganisms, Oct. 20–24, 1996, Bloomington, Ind., (USA), the presence of the dnrV gene has the effect of increasing the conversion from daunorubicin to doxorubicin in Streptomyces.

TABLE 2

Amounts (micrograms/ml) of ε-rhodomycinone, daunorubicin and doxorubicin produced by the *S. peucetius* WMH1658 dnrU::aphII recombinant strain bearing either pWHM3, pWHM299 or pWHM345 in the APM medium at 120 h.

| Strain | ε-rhodomycinone | doxorubicin | daunorubicin | doxo/dauno ratio |
|---|---|---|---|---|
| WMH1658 (pWHM3) | 75.1 | 70.2 | 30.0 | 2.34 |
| WMH1658 (pWHM299) | 60.3 | 49.4 | 44.1 | 1.12 |
| WMH1658 (pWHM345) | 42.8 | 52.1 | 19.3 | 2.70 |

Example 4

Figure 6:
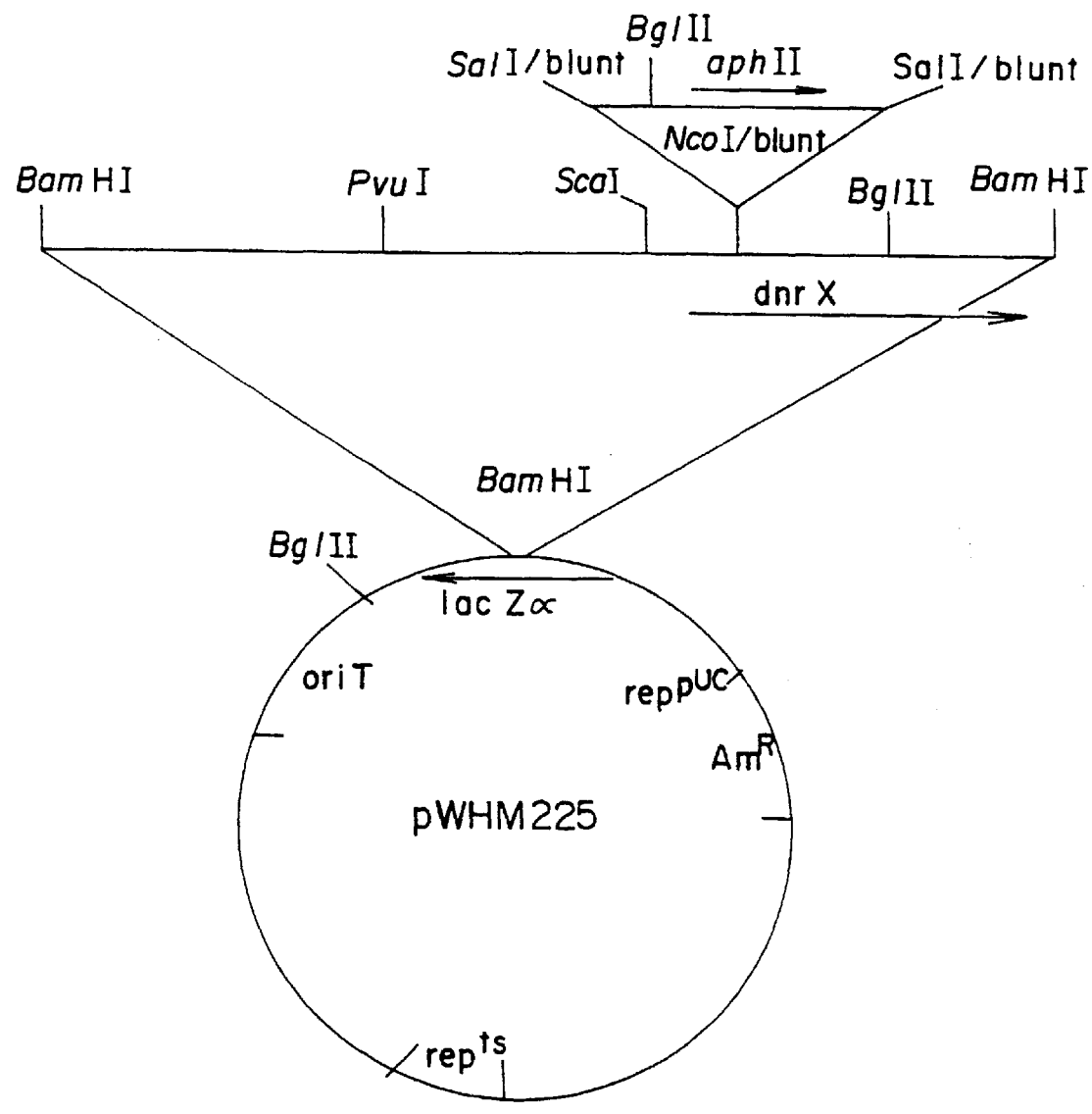
FIG. 6 is a representation of plasmid pWHM225 in which the 4.3 kb EcoRI-HindIII fragment from plasmid pWHM223 is inserted in the EcoRI-HindIII sites of plasmid pKC1139. The construction of plasmid pWHM225 is described in Example 4. The map shown in FIG. 6 does not necessarily provide an exhaustive listing of all restriction sites present in the DNA molecule.

Disruption of dnrX:

pWHM223 is constructed by subcloning the 3.3 kb BamHI fragment obtained from the pWHM335 cosmid clone, described by Stutzman-Engwall and Hutchinson ((Proc. Acad. Sci. USA 86:3135 (1989)) and Otten et al. (J. Bacteriol. 172:3427 (1990)), in the BamHI site of pUC19. This recombinant plasmid is NcoI digested, filled in with the Klenow fragment and ligated with the blunt-ended SalI aphII gene from the pFDNEO-S plasmid described by F. Danis and R. Brzezinski, (FEMS Microbiology Letters 81:261–264 (1991)). This construction is transferred as an EcoRI-HindIII fragment into plasmid pKC1139 (M. Bierman et al., Gene 116:43–49 (1992)) to obtain pWHM225 (FIG. 6). The pKC1139 vector contains a temperature-sensitive replicon that functions well at temperature below 34° C. and bears the apramycin resistance gene. Protoplasts of 29050 strain are transformed with pWHM225, and transformants are selected with apramycin sulfate (40 micrograms/ml) at 30° C. Colonies from this transformation are transferred to ISP4 agar supplemented with kanamycin sulfate (40 micrograms/ml) and incubated at 39° C. for 7 days to eliminate the autonomous replicating vector and to select transformants in which homologous recombination between the cloned DNA and the chromosome has occurred. Three of these cultures are isolated on ISP4 agar with kanamycin sulfate (40 micrograms/ml) and incubated at 39° C. for 7 days. Plates with about 100 colonies are replicated on ISP4 with apramycin sulfate (40 micrograms/ml) and incubated at 39° C. for 7 days. Colonies that don't grow on apramycin are selected from kanamycin plates and checked in fermentation in presence of kanamycin. Two colonies with the kanamycin-resistance, apramycin-sensitive phenotype are examined by Southern analysis to verify the disruption of the dnrX gene. Chromosomal DNA from the 29050 strain and the two dnrX mutants is digested with BamHI and probed with a 500 bp internal fragment of the aphII gene from the pFDNEO-S. The probe hybridizes to 4.3 kb fragment for the two dnrX mutants, which is consistent with the insertion of the aphII resistance gene in the dnrX gene.

Example 5

Enhanced Doxorubicin and Daunorubicin Production and Baumycin-like Compounds Disappearance in Fermentation Broth of dnrX Mutant.

The dnrX mutant is grown for 10 days at 30° C. on slants of ISP4 agar medium added with 40 micrograms/ml of kanamycin sulfate. The spores of this culture are collected and suspended in 300 ml Erlenmeyer flasks containing 25 ml of R2YE liquid medium containing 40 micrograms of kanamycin sulfate and the flasks are shaken for 2 days at 30° C. on a rotary shaker running at 300 rpm in a 5 cm diameter circle. 2.5 ml of this culture are used to inoculate 25 ml of APM medium containing 40 micrograms of kanamycin sulfate in 300 ml Erlenmeyer flasks. The flasks are incubated at 30° C. for 120 hr under the same conditions described for the seed cultures. The metabolites are extracted from the cultures according to the methods described in the Materials and Methods section. The production values are indicated in Tables 3 A and B wherein R.T. stands for Retention Time.

TABLE 3A

Production values in non acidified cultures

| Strain | daunorobicin µg/ml | doxorubicin µg/ml | baumcycin-like R.T. 35.9 | baumcycin-like R.T. 39.3 |
|---|---|---|---|---|
| ATCC 29050 | 6 | 9 | ++ | +++ |
| WMH1654 | 35 | 41 | − | − |

TABLE 3B

Production values in acidified cultures

| Strain | daunorobicin µg/ml | doxorubicin µg/ml | baumcycin-like R.T. 35.9 | baumcycin-like R.T. 39.3 |
|---|---|---|---|---|
| ATCC 29050 | 45 | 14 | − | − |
| WMH1654 | 36 | 41 | − | − |

Example 6

Complementation of the dnrX Mutation with the Wild-type dnrX Gene

To confirm that the disappearance of the baumycin-like products in the fermentation broth is due to dnrX disruption, the dnrX mutant is transformed with the pWHM226 containing, in the BamHI site of the polylinker of pWHM3, the 3.3 kb fragment of the invention including the dnrX. pWHM226 is introduced in the S. peucetius dnrX mutant by the protoplast-mediated transformation method described above, using thiostrepton (50 μg/ml) for selection of the recombinant strains. Transformants are checked for doxorubicin and daunorubicin production, in presence of thiostrepton (10 μg/ml), according to the fermentation conditions described in Materials and Methods. Extracts of the non-acidified fermentation broths of two transformants show in RP-HPLC the appearance of the two peaks with retention times of 35.9 and 39.3 min, respectively, corresponding to the two acid-sensitive, baumycin-like compounds, while extracts of the dnrX mutant fermentation broth obtained under the same conditions do not show these peaks.

Example 7
Construction of a dnrX dnrU Double Mutant

The S.peucetius WMH1654 dnrX mutant strain was infected with a phage integrating vector KC515 derivative that contains a chromosomal fragment with the disrupted copy of dnrU and the aphII gene inserted into a BalI site located at the beginning of the structural part of dnrU. Clones resistant to both neomycin and viomycin were obtained, with the expectation that these clones could be produced by homologous recombination between the cloned fragment and the chromosome of the dnrX mutant. Since the results of PCR analysis indicated that recombination did not take place within the aphII gene in the host, resident in the dnrX gene, and incoming phage DNA, the clones could be a result of homologous recombination in the dnrU gene. Clones resistant to neomycin only were isolated among the progeny of these neomycin and viomycin resistant clones and examined by Southern analysis. When chromosomal DNA from the clones was digested with BamHI and probed with the 1.0 kb PstI-BamHI fragment of pFDNeoS containing the aphII gene, the probe hybridized to 4.3 kb and 7.0 kb BamHI fragments in the DNA from the neomycin resistant mutant, which is consistent with the insertion of the aphII gene into the dnrX and dnrU genes. This strain was named WMH1662 and deposited at the American Type Culture Collection with the accession number ATCC 202051.

Example 8

Additive Effect of dnrX and dnrU Mutations on Doxorubicin Yield

The WMH1662 dnrX dnrU mutant was grown for 10 days at 30° C. on slants of ISP4 agar medium containing 40 micrograms/ml of kanamycin sulfate. The spores of this culture were collected and suspended in 300 ml Erlenmeyer flasks containing 40 micrograms of kanamycin sulfate and the flasks were shaken for 2 days at 30° C. on a rotary shaker running at 300 rpm in a 5 cm diameter circle. A 2.5 ml portion of this culture was used to inoculate 25 ml of APM medium containing 40 micrograms of kanamycin sulfate in 300 ml Erlenmeyer flasks. The flasks were incubated at 30° C. for 120 hr under the same conditions described for the seed cultures. The metabolites were extracted from the cultures according to the methods described above in the Material and Methods section. The amounts of anthracycline metabolites produced are indicated in the following table (Table 4).

TABLE 4

| Strain | Doxorubicin μg/ml | Daunorubicin μg/ml | Rhodomycinone μg/ml | Doxo/Dauno ratio |
|---|---|---|---|---|
| ATCC 29050 | 14.3 | 30.2 | 11.8 | 0.4 |
| dnrX- [WMH1654] | 40.6 | 30.5 | 0 | 1.3 |
| dnrU- [WMH1658] | 47.2 | 15.9 | 69.3 | 2.9 |
| dnrX dnrU [WMH 1662] | 84.8 | 7.0 | 2.4 | 12.1 |

What is claimed is:

1. A recombinant Streptomyces cell which produces doxorubicin, comprising daunorubicin metabolism genes dnrU and dnrX, wherein the dnrU and dnrX genes have been inactivated.

2. The cell according to claim 1, wherein said Streptomyces is *Streptomyces peucetius*.

3. The cell according to claim 2, wherein said cell is WMH 1662.

4. The cell according to claim 1, wherein the daunorubicin metabolism genes are inactivated by insertion of a gene into each daunorubicin metabolism gene.

5. The cell according to claim 4, wherein the daunorubicin metabolism genes are inactivated by insertion of a neomycin/kanamycin resistance gene aphII.

6. A process for preparing at least one compound selected from the group consisting of daunorubicin and doxorubicin, comprising the steps of:
    culturing a recombinant Streptomyces cell comprising daunorubicin metabolism genes dnrX and dnrU, wherein the dnrX and dnrU genes have been inactivated and
    isolating at least one compound selected from the group consisting of daunorubicin and doxorubicin from the culture.

7. The process according to claim 6, wherein said Streptomyces is *Streptomyces peucetius*.

8. The process according to claim 7, wherein said Streptomyces peucetius is WMH 1662.

9. A vector comprising one daunorubicin metabolism gene dnrX, wherein the daunorubicin metabolism gene has been inactivated.

10. The vector according to claim 9, wherein the dnrX gene is inactivated by insertion of an aphII gene.

11. The vector according to claim 9, wherein said vector is a plasmid.

12. The vector according to claim 9, wherein the vector is a phage.

13. A host cell transformed with the vector according to claim 9.

14. A host cell comprising daunorubicin metabolism genes, wherein a first daunorubicin metabolism gene, selected from the group consisting of dnrU gene and dnrX gene is inactivated by insertion of another gene, and wherein said host cell is transformed with a vector comprising a second daunorubicin metabolism gene selected from the group consisting of the dnrU gene and the dnrX gene, wherein said second gene is not said first gene and wherein said second gene is inactivated by the insertion of another gene.

15. A host cell comprising daunorubicin metabolism genes, wherein a dnrU daunorubicin gene is inactivated by insertion of another gene and wherein said host cell is transformed with a vector comprising dnrX daunorubicin metabolism gene wherein said dnrX gene is inactivated by the insertion of another gene.

16. A host cell comprising daunorubicin metabolism genes, wherein a dnrX daunorubicin gene is inactivated by insertion of another gene and wherein said host cell is transformed with a vector comprising dnrU daunorubicin metabolism gene wherein said dnrU gene is inactivated by the insertion of another gene.

* * * * *